United States Patent [19]

Hostettler et al.

[11] Patent Number: 5,171,354
[45] Date of Patent: Dec. 15, 1992

[54] HETEROCYCLIC COMPOUNDS

[75] Inventors: Bernhard Hostettler, Zurich, Switzerland; Ludwig R. Wälder, Jestetten-Altenburg, Fed. Rep. of Germany

[73] Assignee: Ciba-Geigy Corporation, Ardsley, N.Y.

[21] Appl. No.: 656,271

[22] Filed: Feb. 15, 1991

[30] Foreign Application Priority Data

Feb. 16, 1990 [CH] Switzerland .......................... 511/90

[51] Int. Cl.$^5$ ............................................. A01N 43/40
[52] U.S. Cl. ................................................. 71/94; 71/88
[58] Field of Search ........................... 71/94; 546/338

[56] References Cited

U.S. PATENT DOCUMENTS 4,605,656  8/1986  Dorn .................................. 514/255

FOREIGN PATENT DOCUMENTS 2117768A  10/1983  United Kingdom .
2117772    10/1983  United Kingdom .

OTHER PUBLICATIONS

J. Amer. Chem. Soc. 70, 4187-9 (1948).

*Primary Examiner*—Richard L. Raymond
*Assistant Examiner*—John D. Pak
*Attorney, Agent, or Firm*—Kevin T. Mansfield; Edward McC. Roberts

[57] ABSTRACT

Herbicides are described which comprise herbicidally active compounds of the formula

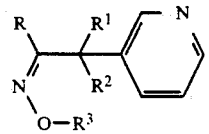

in which R, $R^1$, $R^2$ and $R^3$ have the meanings indicated in the description, their N-oxides and the acid addition salts of the compounds I or their N-oxides, and the use of these substances and of the compositions are described. Certain novel compounds of the formula I, N-oxides and acid addition salts and their preparation are also described.

8 Claims, No Drawings

HETEROCYCLIC COMPOUNDS

The present invention relates to herbicides which contain herbicidally active heterocyclic compounds. These compounds are 2-(3-pyridyl)acetophenone oximes of the general formula

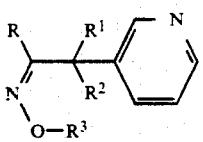

I in which R is a substituted or unsubstituted phenyl group of the formula

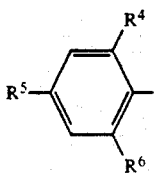

(a)

$R^1$ and $R^2$ independently of one another are hydrogen, $C_n$alkyl, $C_n$alkenyl or $C_n$alkynyl, where n is a number from 1–4 and $R^1$ or $R^2$ are hydrogen if n is greater than 2, $R^3$ is hydrogen; $C_{1-10}$alkyl, $C_{3-10}$alkoxyalkyl or $C_{3-10}$alkylthioalkyl each containing an alkylene chain of at least two carbon atoms; aryl; aryl-$C_{1-3}$alkyl; $C_{3-6}$alkenyl; $C_{3-6}$alkynyl; or a group

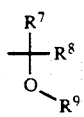

(b)

$R^4$ is hydrogen or fluorine, $R^5$ and $R^6$ independently of one another are hydrogen, halogen, $C_{1-4}$alkyl or trifluoromethyl, $R^7$ and $R^8$ independently of one another are hydrogen, $C_{1-6}$alkyl, $C_{3-6}$alkenyl or $C_{3-6}$alkynyl or $R^7$ and $R^8$ together are tetra- or pentamethylene which is unsubstituted, monosubstituted or polysubstituted by $C_{1-3}$alkyl, and $R^9$ is $C_{1-10}$alkyl; $C_{3-6}$(alkoxyalkyl) or $C_{3-6}$(alkylthioalkyl) each containing an alkylene chain of at least two carbon atoms; aryl-$C_{1-3}$alkyl; $C_{3-6}$cycloalkyl which is unsubstituted, monosubstituted or polysubstituted by $C_{1-3}$alkyl; $C_{3-10}$alkenyl; $C_{3-10}$alkynyl; or aryl, or $R^7$ is hydrogen and $R^8$ and $R^9$ together are tetramethylene which is unsubstituted, monosubstituted or polysubstituted by $C_{1-3}$alkyl, where the group (b) is not intended to include the $C_{3-10}$alkoxyalkyl group already defined above in $R^3$, their N-oxides and the acid addition salts of the compounds I and the corresponding N-oxides.

In the above formula I, "halogen" in each case includes fluorine, chlorine, bromine and iodine. The alkyl, alkenyl and alkynyl radicals can be straight-chain or branched, this also applying to the alkyl, alkenyl or alkynyl moiety of the arylalkyl groups, and possible other alkyl-, alkenyl- or alkynyl-containing groups. "Aryl" is to be understood in particular as meaning phenyl. Such aromatic groups can have one or more identical or different substituents, for example halogen, hydroxyl, $C_{1-3}$alkyl (in particular methyl), $C_{1-3}$alkoxy (in particular methoxy), trifluoromethyl, nitro and/or cyano. This also applies to the aryl moiety of an aryl-containing group, such as arylalkyl.

In the case of $C_{3-10}$alkylthioalkyl, $C_{3-10}$alkoxyalkyl, or of $C_{3-6}$(alkylthioalkyl) or $C_{3-6}$(alkoxyalkyl) groups, the expression "alkylene chain" used in this connection is the chain of carbon atoms which extends between the sulfur or oxygen atom of the respective group and the free bond. Examples of such groups are 2-methylthioethyl, 3-methoxypropyl and 2-methylthiopropyl (the first- and third-mentioned groups have an alkylene chain of 2 carbon atoms, the second-mentioned one of 3 carbon atoms).

Asymmetric carbon atoms can be present in compounds of the formula I, so that the compounds can be present as enantiomer or diastereomer mixtures. Geometric isomerism occurs owing to the presence of the C=N double bond and, if applicable, also of an aliphatic C=C double bond. The formula I is accordingly intended to include all these possible isomeric forms and the isomer mixtures.

Suitable acid addition salts of the compounds I are physiologically tolerable salts. These preferably include salts of the compounds I with inorganic or organic acids such as hydrochloric acid, nitric acid, phosphoric acid, mono- and bifunctional carboxylic acids and hydroxycarboxylic acids, for example acetic acid, maleic acid, succinic acid, fumaric acid, tartaric acid, citric acid, salicylic acid, sorbic acid and lactic acid, and sulfonic acids, for example 1,5-naphthalenedisulfonic acid. In the case of the N-oxides, i.e. the compounds of the formula I in which the 3-pyridyl group carries an oxygen atom (N→O), suitable acid addition salts are in particular physiologically tolerated salts with strong acids, such as inorganic acids, for example hydrochloric acid, nitric acid and phosphoric acid, and sulfonic acids, for example 1,5-naphthalenedisulfonic acid.

Independently of one another, R is preferably 2,4- or 2,6-dihalophenyl, in particular 2-chloro-4-fluorophenyl, 4-chloro-2-fluorophenyl, 2,4-dichlorophenyl, 2-chloro-6-fluorophenyl or 2,6-difluorophenyl, of which 2-chloro-4-fluorophenyl and 2,6-difluorophenyl and also 2-chloro-6-fluorophenyl are particularly preferred groups (a); $R^1$ or $R^2$ is preferably hydrogen and $R^2$ and/or $R^1$ is hydrogen or alkyl, in particular hydrogen or methyl, and $R^3$ is preferably tert-butyl or a group (b) in which $R^7$, $R^8$ and $R^9$ independently of one another are $C_{1-10}$alkyl, in particular all three are methyl or $R^7$ is ethyl, $R^8$ is n-propyl and $R^9$ is methyl.

Particularly preferred compounds of the formula I are:

2',4'-dichloro-2-(3-pyridyl)acetophenone O-(tert-butyl)oxime,

2',4'-dichloro-2-(3-pyridyl)acetophenone O-(1-methoxy-1-methylethyl)oxime,

2'-chloro-4'-fluoro-2-(3-pyridyl)acetophenone O-(1-methoxy-1-methylethyl)oxime

2',6'-difluoro-2-(3-pyridyl)acetophenone O-(1-methoxy-1-methylethyl)oxime

4'-chloro-2'-fluoro-2-(3-pyridyl)acetophenone O-(1-methoxy-1-methylethyl)oxime and 2'-chloro-4'-fluoro-2-(3-pyridyl)acetophenone O-(1-ethyl-1-methoxy-n-butyl)oxime.

Other representatives of compounds I are:

2',4'-dichloro-2-methyl-2-(3-pyridyl)propiophenone O-(1-methoxy-1-methylethyl)oxime, 2'-chloro-4'-fluoro-2-methyl-2-(3-pyridyl)propiophenone O-(1-methoxy-1-methylethyl)oxime,
2',4'-dichloro-2-(3-pyridyl)acetophenone O-(1-ethoxyethyl)oxime,
2'-chloro-4'-fluoro-2-(3-pyridyl)acetophenone O-(1-ethoxyethyl)oxime,
2',4'-dichloro-2-(3-pyridyl)acetophenone O-(1-methoxyethyl)oxime,
2'-chloro-4'-fluoro-2-(3-pyridyl)acetophenone O-(1-methoxyethyl)oxime,
2',4'-dichloro-2-(3-pyridyl)acetophenone O-(1-methoxypropyl)oxime,
2'-chloro-4'-fluoro-2-(3-pyridyl)acetophenone O-(1-methoxypropyl)oxime,
2',4'-dichloro-2-(3-pyridyl)propiophenone O-methoxymethyloxime,
2'-chloro-4'-fluoro-2-(3-pyridyl)propiophenone O-methoxymethyloxime,
2',4'-dichloro-2-(3-pyridyl)acetophenone O-(1-methoxycyclohexyl)oxime,
2',4'-dichloro-2-(3-pyridyl)acetophenone O-(2-tetrahydropyranyl)oxime and
2'-chloro-4'-fluoro-2-(3-pyridyl)acetophenone O-(2-tetrahydropyranyl)oxime.

In general, the (E) isomers are distinguished as more effective herbicides than the (E/Z) isomer mixtures which, in turn, have a higher herbicidal activity than the (Z) isomers.

Some of the compounds of the formula I and their N-oxides and acid addition salts are novel and some are known, see, for example, European Patent Application EP-A-0 049 854 and German Offenlegungsschriften DE-OS 3 309 466 and 3 310 148, which comprise the known compounds and their properties as fungicides. The novel compounds can accordingly be defined as follows:
compounds of the general formula

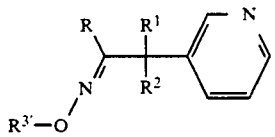

in which R, $R^1$ and $R^2$ have the meanings indicated under formula I and $R^{3'}$ is $C_{3-10}$(alkylthioalkyl) having an alkylene chain of at least two carbon atoms, or a group (b) as this is defined above,
their N-oxides and the acid addition salts of the compounds I' and their N-oxides.

The present invention also relates to these novel compounds of the formula I', and to their N-oxides and acid addition salts and to the process for the preparation of these novel compounds.

The mainly known compounds of the formula I, i.e. those compounds of the formula I in which R, $R^1$ and $R^2$ have the meanings indicated above and $R^3$ is hydrogen; $C_{1-10}$alkyl; $C_{3-10}$alkoxyalkyl; aryl; aryl-$C_{1-3}$alkyl; $C_{3-6}$alkenyl; or $C_{3-6}$alkynyl, and their N-oxides and the acid addition salts of these compounds can be prepared by the methods described in European Patent Publication EP-A-0 049 854 and in German Offenlegungschriften 3 309 466 and 3 310 148 or in an analogous manner.

The process according to the invention for the preparation of the novel compounds of the formula I', N-oxides and acid addition salts comprises a) for the preparation of those compounds of the formula I' in which $R^1$ and $R^2$ are hydrogen and $R^{3'}$ is different from a group (b), reacting an enamine of the general formula

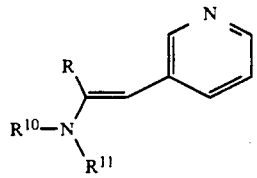

in which R has the abovementioned meaning and $R^{10}$ and $R^{11}$ independently of one another are $C_{1-4}$alkyl, in particular methyl or ethyl,
with an O-substituted hydroxylamine of the general formula

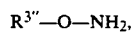

$$R^{3''}-O-NH_2,\qquad\text{III}$$

in which $R^{3''}$ is $C_{1-10}$alkyl; $C_{3-10}$alkoxyalkyl or $C_{3-10}$alkylthioalkyl each having an alkylene chain of at least 2 carbon atoms; aryl; aryl-$C_{1-3}$alkyl; $C_{3-6}$alkenyl; or $C_{3-6}$alkynyl, or with an inorganic acid addition salt thereof, b) for the preparation of those compounds of the formula I' and of their N-oxides in which $R^{3'}$ is different from a group (b), reacting an acetophenone derivative or its N-oxide of the general formula

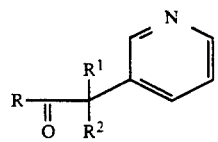

in which R, $R^1$ and $R^2$ have the abovementioned meanings, with an O-substituted hydroxylamine of the general formula III indicated above or with an inorganic acid addition salt thereof or with hydroxylamine hydrochloride, c) for the preparation of those compounds of the formula I' in which $R^{3'}$ is different from a group (b) and of their N-oxides, reacting an oxime or its N-oxide of the general formula

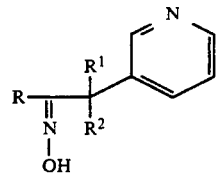

in which R, $R^1$ and $R^2$ have the meanings indicated above, with a compound of the general formula

$$R^{3'''}-X\qquad\text{VI}$$

in which $R^{3'''}$ is $C_{3-6}$(alkylthioalkyl) or $C_{3-6}$(alkoxyalkyl) having an alkylene chain of at least two carbon atoms; aryl-$C_{1-3}$alkyl; $C_{3-6}$cycloalkyl which is unsubstituted, monosubstituted or polysubstituted by $C_{1-3}$alkyl; $C_{3-10}$alkenyl; or $C_{3-10}$alkynyl; and X is a leaving group, for example chlorine, bromine, iodine, mesyloxy, tosyloxy or an alkylsulfate radical, d) for the preparation of those compounds of the formula I' and of their N-oxides in which R³' is a group (b) in which, however, R⁸ and R⁹ are not linked to one another, reacting an oxime of the general formula V indicated above or its N-oxide with a diether of the general formula

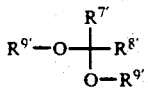   VII in which R⁷', R⁸' and R⁹' have the individual meanings of R⁷, R⁸ or R⁹ indicated above and, in addition, R⁷' and R⁸' together can be tetra- or pentamethylene which is unsubstituted, monosubstituted or polysubstituted by C₁₋₃alkyl, or e) for the preparation of those compounds of the formula I' and of their-oxides in which R³' is a group (b) in which R⁷ is hydrogen and R⁸ and R⁹ are together tetramethylene which is unsubstituted, monosubstituted or polysubstituted by C₁₋₃alkyl, reacting an oxime of the general formula V indicated above or its N-oxide with a compound of the general formula

   VIII in which Y is trimethylene which is unsubstituted, monosubstituted or polysubstituted by C₁₋₃alkyl.

The reaction according to process variant a) expediently takes place in a strongly acidic, aqueous diluent, such as sulfuric acid, at temperatures between 0° C. and 100° C., preferably at 60°–75° C. If the hydroxylamine is employed as an acid addition salt thereof, this is suitable a salt with an inorganic acid, preferably the hydrochloride.

Process variant b) is expediently carried out by reacting the acetophenone derivative of the formula IV or its N-oxide with the hydroxylamine of the formula III, or with an acid addition salt thereof, preferably the hydrochloride or hydrosulfate, in an organic solvent, for example an alcohol, such as methanol or ethanol, a dialkylamide, such as dimethylformamide, or a tertiary amine, such as pyridine. The reaction is preferably carried out in a temperature range between room temperature and the reflux temperature of the reaction mixture. As the hydroxylamine III is preferably employed in the form of an acid addition salt, for example the hydrochloride or hydrosulfate, a base, such as sodium carbonate or potassium carbonate, triethylamine or pyridine is expediently added to the reaction mixture.

Using a compound of the formula VI as a reagent, process variant c) can be carried out by reacting the oxime of the formula V or its N-oxide with the compound of the formula VI, expediently in the presence of a base, in an organic solvent and in a temperature range between 0° C. and the reflux temperature of the reaction mixture. The solvent can be protic or non-protic. In the case of protic solvents, such as alcohol, in particular methanol or ethanol, the base used is preferably an alkali metal hydroxide, for example sodium hydroxide or potassium hydroxide, or an alkali metal alkoxide. When using non-protic solvents, such as aliphatic or cyclic ethers, in particular 1,2-dimethoxyethane or tetrahydrofuran, and dialkylamides, in particular dimethylformamide, the base is preferably an alkali metal hydride, for example sodium hydride. In a preferred embodiment of this process, sodium hydride is used as the base and an aliphatic or cyclic ether, in particular tetrahydrofuran or dimethoxyethane, or a dialkylamide, in particular dimethylformamide, as the solvent.

Process variant d) is expediently carried out using the diether of the formula VII both as a reagent and as a solvent. The reaction is suitably carried out at temperatures between room temperature and the reflux temperature of the reaction mixture and in the presence of a catalytic amount of an aprotic acid, for example methanesulfonic acid, p-toluenesulfonic acid or a strongly acidic synthetic resin, for example Amberlyst ® A15. As an alternative, the oxime V or its N-oxide can be reacted with 1 to 5 equivalents, preferably about 2 equivalents, of the diether VII, in the presence of a polar cosolvent, for example of a xylene, 1,3-dimethyl-3,4,5,6-tetrahydro-2(1H)pyrimidinone or in particular dioxane, at temperatures between 0° C. and the reflux temperature of the reaction mixture, preferably at about 90°–100° C.

The reaction according to process variant e) is expediently carried out using the compound of the formula VIII both as a reagent and as a solvent, at temperatures between 0° C. and 50° C., in particular at room temperature, and in the presence of a catalytic amount of a mineral acid, for example hydrochloric acid. Further details of this type of reaction are found in J.A.C.S. 70, 4187 (1948).

The N-oxidation of a final product of the formula I, if not already present in the form of the N-oxide, can expediently be carried out by oxidising the compound of the formula I' by means of a peracid in the presence of an inert diluent. Compounds of the formula I' in which R³' is a group (b) cannot be N-oxidised (in such cases it is already possible to prepare the N-oxides in process variant d) or e), i.e. using an N-oxide of the oxime of the formula V).

Suitable peracids are preferably peracetic acid, perbenzoic acid and m-chloroperbenzoic acid, the reaction preferably being carried out in a halogenated hydrocarbon, for example methylene chloride or chloroform, as a diluent. N-Oxidation with a peracid is preferably carried out in a temperature range between 0° C. and the reflux temperature of the reaction mixture, in particular between 0° C. and room temperature. A particularly preferred embodiment of this process comprises carrying out the N-oxidation with m-chloroperbenzoic acid in chloroform in a temperature range between 0° C. and room temperature.

To prepare acid addition salts, the compounds of the formula I' or their N-oxides with inorganic or organic acids, for example hydrochloric acid, nitric acid, phosphoric acid, mono- and bifunctional carboxylic acids and hydroxycarboxylic acids or sulfonic acids, can be reacted, if desired, in a manner known per se. As a rule, however, those compounds of the formula I in which R³' is a group (b) cannot be converted into their acid addition salts, as they are particularly acid-sensitive.

The compounds of the formula I', N-oxides or acid addition salts thus prepared are isolated and purified by methods which are known per se.

The compounds of the formulae II–Iv, VII–VIII and N-oxides of the compounds IV and V and inorganic acid addition salts of the compounds III which can be used as starting materials are either known or can be prepared by methods known per se. The compounds of the formula V which can be used as starting materials are a sub-group of largely known compounds of the formula I (see, for example, EP-A-0 049 854 and DE-OS 3 310 148).

The compounds of the formula I, N-oxides and acid addition salts (overall designated as "active ingredients" in the following) have herbicidal properties and are suitable for controlling weeds, including grass weed, inter alia *Agropyron repens, Alopecurus myosuroides, Digitaria sanguinalis, Bromus inermis, Echinochloa crus-galli, Poa annua, Sorghum halepense, Abutilon theophrasti, Amaranthus retroflexus, Chrysanthemum segetum, Sinapis arbensis* and *Stellaria media*, in diverse useful plant crops, inter alia crops of *Oryza sativa* (rice), *Triticum aestivum* (wheat), *Zea mays* (maize), *Beta vulgaris* (sugar beet), *Brassica napus* (rape), *Glycine max* (soya) and *Gossypium hirsutum* (cotton). In addition, the active ingredients are both pre-emergence and post-emergence herbicides. A very good selectivity has been shown in the case of some representatives of the active ingredients, in particular in the control of weeds in paddy rice crops. In these, concentrations of the active ingredients are tolerated by various rice varieties, for example Koshihikari and Labelle, which are considerably above the dosages by which the most important rice weeds, including grass weeds, are controlled. Examples of such weeds found in rice crops are *Echinochloa crus-galli, Echinochloa caudata, Monochoria vaginalis, Lindernia procumbens, Sagittaria pygmaea, Scirpus juncoides* and *Cyperus serotinus*.

In practice, a concentration of 1 g to 3 kg of active ingredient/ha, preferably 10 g to 1 kg of active ingredient/ha, is customarily sufficient to achieve the desired herbicidal effect. To achieve the desired herbicidal effect together with optimum useful-plant tolerability, the range from 10 to 300 g/ha in pre-emergence treatment and from 300 to 3000 g/ha in post-emergence treatment is particularly favourable.

The herbicide according to the invention comprises an effective amount of at least one compound of the formula I, as defined above, of an N-oxide thereof or of an acid addition salt of such a compound I or such an N-oxide, and also formulation auxiliaries. The composition expediently contains at least one of the following formulation auxiliaries from the group comprising: solid carriers; solvents or dispersants; surfactants (wetting agents and emulsifiers); dispersants (without surfactant action); and stabilisers. Using these and other auxiliaries, these compounds, i.e. the herbicidal active ingredients, can be converted into the customary formulations, such as dusts, powders, granules, solutions, emulsions, suspensions, emulsifiable concentrates, pastes and the like.

The compounds of the formula I and their N-oxides are in general water-insoluble, the acid addition salts, on the other hand, are water-soluble, and can be formulated by the methods customary for water-insoluble or water-soluble compounds using the relative formulation auxiliaries. The compositions can be produced in a manner known per se, for example by mixing the respective active ingredient with solid carriers, by dissolving or suspending it in suitable solvents or dispersants, possibly using surfactants as wetting agents or emulsifiers and/or dispersants, by diluting already prepared emulsifiable concentrates with solvents or dispersants etc.

Suitable solid carriers are in the main: natural minerals, such as chalk, dolomite, limestone, aluminas and silica and their salts (for example kieselguhr, kaolin, bentonite, talc, attapulgite and montmorillonite); synthetic minerals, such as highly disperse silica, alumina and silicates; organic materials, such as cellulose, starch, urea and synthetic resins; and fertilisers, such as phosphates and nitrates, it being possible for such carriers to be present, for example, as powders or as granules.

Suitable solvents or dispersants are in the main: aromatic compounds and chlorinated aliphatic hydrocarbons, such as chlorobenzenes, chloroethylenes and methylene chloride; aliphatic hydrocarbons, such as cyclohexane and paraffins, for example mineral oil fractions; alcohols, such as butanol and glycol, and their ethers and esters; ketones, such as acetone, methyl ethyl ketone, methyl isobutyl ketone and cyclohexanone; and strongly polar solvents or dispersants, such as dimethylformamide, N-methylpyrrolidone and dimethyl sulfoxide, such solvents preferably having flash points of at least 30° C. and boiling points of at least 50° C., and water. Among the solvents and dispersants, those which are also suitable include so-called liquefied gaseous extenders or carriers, which are products which are gaseous at room temperature and under normal pressure. Examples of such products are in particular aerosol propellent gases (such as halohydrocarbons, for example dichlorodifluoromethane or other neutral propellent gases. If the herbicide according to the invention is present in the form of a pressurised gas pack, a solvent is expediently used in addition to the propellent gas.

The surfactants (wetting agents and emulsifiers) can be non-ionic compounds, such as condensation products of fatty acids, fatty alcohols or fat-substituted phenols with ethylene oxide; fatty acid esters and ethers of sugars or polyhydric alcohols; the products which are obtained from sugars or polyhdric alcohols by condensation with ethylene oxide; block polymers of ethylene oxide and propylene oxide; or alkyldimethylamine oxides.

The surfactants can also be anionic compounds, such as soaps; fatty sulfate esters, for example sodium dodecyl sulfate, sodium octadecyl sulfate and sodium cetyl sulfate; alkylsulfonates, arylsulfonates and fatty aromatic sulfonates, such as alkylbenzenesulfonates, for example calcium dodecylbenzenesulfonate, and butylnaphthalenesulfonates; and more complex fatty sulfonates, for example the amide condensation products of oleic acid and N-methyltaurine and the sodium sulfonate of dioctyl succinate.

The tensides can finally be cationic compounds, such as alkyldimethylbenzylammonium chlorides, dialkyldimethylammonium chlorides, alkyltrimethylammonium chlorides and ethoxylated quaternary ammonium chlorides.

Suitable dispersants (without surfactant action) are in the main: lignin, sodium and ammonium salts of ligninsulfonic acids, sodium salts of maleic anhydride/diisobutylene copolymers, sodium and ammonium salts of sulfonated polycondensation products of naphthalene and formaldehyde, and sulfite waste liquors.

Dispersants, which are suitable in particular as thickeners and anti-settling agents, which can be employed are, for example, methylcellulose, carboxymethylcellulose, hydroxyethylcellulose, polyvinyl alcohol, alginates, caseinates and blood albumin.

Examples of suitable stabilisers are acid-binding agents, for example epichlorohydrin, phenyl glycidyl ether and epoxidised soya oils; antioxidants, for example gallic acid esters and butylhydroxytoluene; UV absorbers, for example substituted benzophenones, diphenylacrylic acid esters and cinnamic acid esters; and deactivators, for example salts of ethylenediaminetetraacetic acid and polyglycols.

The herbicides according to the invention can contain synergists and other active ingredients, for example insecticides, acaricides, fungicides, plant growth regulators and fertilisers, in addition to the active ingredients. Such combination agents are suitable for increasing the activity or for widening the activity spectrum.

The herbicides according to the invention in general contain between 0.001 and 99 percent by weight, preferably between 0.1 and 90 percent by weight of one or more active ingredients of the formula I, 1-99% of a solid or liquid additive, for example solid carriers, solvents and dispersants and also stabilisers and 0 to 25% of a surfactant. They can be present, for example, in a form which is suitable for storage and transport. In such formulations, for example emulsifiable concentrates, the active ingredient concentration is normally in the higher range, preferably between 5 and 80 percent by weight, in particular between 10 and 50 percent by weight. These formulations can then be diluted, for example with identical or different inert substances, to active ingredient concentrations which are suitable for practical use, i.e. preferably about 0.001 to 10 percent by weight, in particular about 0.01 to 5 percent by weight. However, the active ingredient concentrations can also be smaller or larger.

As mentioned above, the production of the herbicides according to the invention can be carried out in a manner known per se.

For the production of pulverulent preparations, the active ingredient or the active ingredients can be mixed with solid carrier, for example by grinding together; or the solid carrier can be impregnated with a solution or suspension of the active ingredient and the solvent or dispersant can then be removed by evaporating, heating or aspirating under reduced pressure. By addition of surfactants or dispersants, such pulverulent compositions can be made easily wettable with water, so that they can be converted into aqueous suspensions which, for example, are suitable as spray compositions.

The active ingredient can also be mixed with a surfactant and a solid carrier to form a wettable powder which is dispersible in water, or it can be mixed with a solid pregranulated carrier to form a granular product.

If desired, the active ingredient can be dissolved in a water-immiscible solvent, for example a high-boiling hydrocarbon, which expediently contains dissolved emulsifier, so that the solution is self-emulsifying on adding to water. On the other hand, the active ingredient can be mixed with an emulsifier and the mixture can then be diluted with water to the desired concentration. In addition, the active ingredient can be dissolved in a solvent and then mixed with an emulsifier. Such a mixture can also be diluted with water to the desired concentration. Emulsifiable concentrates or ready-to-use emulsions are obtained in this manner.

The use of the herbidicides according to the invention, which forms a further subject of the present invention, can be carried out by customary application methods, such as atomising, spraying, dusting, pouring or scattering. The method according to the invention for the control of weeds comprises treating the material to be protected against weeds and/or the weeds with a compound of the formula I, an N-oxide thereof or an acid addition salt of the compound I or its N-oxide or with a herbicide according to the invention.

The following examples serve to illustrate the invention in more detail.

I. Preparation of the active ingredients

EXAMPLE 1

A solution of 1.2 g of O-methylhydroxylamine hydrochloride in 2.4 ml of distilled water is slowly treated with concentrated sulfuric acid with stirring in such a way that the reaction temperature does not rise above 60° C. 4.0 g of 3-[β-(diethylamino)-2-chloro-4-fluorostyryl]pyridine are then added rapidly in such a way that the internal temperature is exactly 70° C. at the end of the addition. The mixture is then stirred at 70° C. for 5 hours, cooled to room temperature and poured into ice-water. The aqueous phase is adjusted to pH=8.0 with sodium hydroxide solution and the mixture is extracted with diethyl ether. The organic phase is dried over anhydrous magnesium sulfate and concentrated under reduced pressure. 2'-Chloro-4'-fluoro-2-(3-pyridyl)acetophenone O-methyloxime is obtained as an E/Z isomer mixture in the form of a brownish oil. Column chromatographic separation on silica gel using n-hexane/ethyl acetate (4:1) first gives the E isomer [$^1$H-NMR (CDCl$_3$, 200 MHz): 4.03 ppm (s, C$\underline{H}_3$O—N=)] and then the Z isomer [$^1$H-NMR (C$\overline{D}$Cl$_3$, 200 MHz): 3.84 ppm (s, C$\underline{H}_3$O—N=)].

EXAMPLE 2

A solution of 4.65 g of 2',4'-dichloro-2-(3-pyridyl)acetophenone in 25 ml of ethanol is treated with 2.70 g of anhydrous sodium carbonate and 2.63 g of O-isobutylhydroxylamine hydrochloride and the reaction mixture is then heated to reflux temperature with stirring. After 4 hours, it is poured onto ice and extracted with ethyl acetate. The organic phase is washed with water, dried over anhydrous magnesium sulfate and concentrated under reduced pressure. 2',4'-Dichloro-2-(3-pyridyl)acetophenone O-isobutyloxime is obtained as an E/Z isomer mixture in the form of a brownish oil. In the chromatographic separation on silica gel using n-hexane/ethyl acetate (7:3), the E isomer [$^1$H-NMR (CDCl$_3$, 200 MHz): 2.055 ppm (heptet, $\underline{H}$C(CH$_3$)$_2$)] is eluted first and then the Z isomer [$^1$H-N$\overline{M}$R (CDCl$_3$, 200 MHz): 1.928 ppm (heptet, $\underline{H}$C(CH$_3$)$_2$)].

EXAMPLE 3

A solution of 3.6 g of 2',4'-dichloro-2-methyl-2-(3-pyridyl)acetophenone in 15 ml of ethanol and 4 ml of water is treated with 1.4 g of hydroxylamine hydrochloride, 3 ml of pyridine and 90 mg of 4-N,N-dimethylaminopyridine and the reaction mixture is heated to reflux temperature. After 16 hours, it is poured into ice-water and extracted with ethyl acetate. The organic phase is dried over anhydrous magnesium sulfate and concentrated under reduced pressure. The crystalline crude product is recrystallised from methylene chloride/n-hexane. 2',4'-Dichloro-2-methyl-2-(3-pyridyl)acetophenone oxime is obtained as an E/Z isomer mixture in the form of beige crystals, m.p. 163°-165° C.

EXAMPLE 4

A solution of 2',4'-difluoro-2-(3-pyridyl)acetophenone oxime in 25 ml of dimethoxyethane is treated in portions with 0.50 g of sodium hydride dispersion (55% in oil) and the mixture is stirred at room temperature for 30 minutes. 1.8 g of methyl iodide is then added and the mixture is heated to reflux temperature. After 4 hours, it is cooled to room temperature, poured onto ice and extracted with ethyl acetate, and the organic phase is dried over anhydrous magnesium sulfate and concentrated under reduced pressure. After separation by column chromatography on silica gel, (E)-2',4'-difluoro-2-(3-pyridyl)acetophenone O-methyloxime [$^1$H-NMR (CDCl$_3$, 200 MHz): 4.05 ppm (s, CH$_3$O—N=)] is obtained first and then (Z)-2',4'-difluoro-2-(3-pyridyl)acetophenone O-methyloxime [$^1$H-NMR (CDCl$_3$, 200 MHz): 3.91 ppm (s, C$\underline{H}_3$O—N=)].

EXAMPLE 5

A solution of 20.00 g of 2'-chloro-6'-fluoro-2-(3-pyridyl)acetophenone oxime is dissolved in 170 ml of 2,2-dimethoxypropane and, after adding 0.5 g of pulverised Amberlyst ® A15, the mixture is heated to reflux temperature with stirring. After 12–14 hours in each case, about 30 ml of the reaction mixture are removed by distillation and replaced by the same amount of 2,2-dimethoxypropane. After 48 hours, starting material can no longer be detected by thin layer chromatography. The reaction mixture is cooled to about 40° C. and concentrated to about one third of the original volume at 80 mbar on a rotary evaporator at this temperature after filtration through Celite ®. The residue is poured into 150 ml of ice-water and extracted three times with 150 ml of diethyl ether each time. The combined ether phases are washed once with 200 ml of water, dried over anhydrous magnesium sulfate and evaporated. 2'-Chloro-4'-fluoro-2-(3-pyridyl)acetophenone O-(1-methoxy-1-methylethyl)oxime is obtained as an E/Z isomer mixture in the form of a yellow oil. After silica gel chromatography using n-hexane/ethyl acetate (3:2), the E isomer [$^1$H-NMR (CDCl$_3$, 200 MHz): 4.08 ppm (s, H$_3$C—O—C)] is obtained first and then the Z isomer [$^1$H-NMR (CDCl$_3$, 200 MHz): 3.97 ppm (s, H$_3$C—O—C)].

EXAMPLE 6

A solution of 7.45 g of 2',6'-difluoro-2-(3-pyridyl)acetophenone oxime in 170 ml of xylene is mixed with 8.00 g of diethoxypropane and then heated to 80° C. with stirring. After a clear solution has formed, 0.20 g of pulverised Amberlyst ® A15 is added and the entire mixture is heated to reflux temperature. After 6 hours, the reaction mixture is subjected to clarifying filtration through Celite ® and the filtrate is freed of excess solvent at 60° C. in a water jet vacuum. After drying in a high vacuum, 2',6'-difluoro-2-(3-pyridyl)acetophenone O-(1-ethoxy-1-methylethyl)oxime is obtained as an E/Z isomer mixture in the form of a yellow oil. On chromatographic separation on silica gel using n-hexane/ethyl acetate (3:1), the E isomer [$^1$H-NMR (CDCl$_3$, 200 MHz): 1.428 ppm (s, —C(CH$_3$)$_2$)] is obtained first in the form of slightly yellowish oils.

EXAMPLES 7–41

The compounds of the formula I shown in Table 1 below are prepared from the corresponding starting materials analogously to the process described in Example 1,2,3,4,5 or 6.

TABLE 1

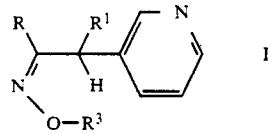

| Example | R | R$^1$ | R$^3$ | Physical data | Method of Example |
|---|---|---|---|---|---|
| 7 | Phenyl | hydrogen | hydrogen | white solid | 2 |
| 8 | 2,4-Dichlorophenyl | hydrogen | hydrogen | white solid | 2 |
| 9 | α,α,α-Trifluoro-o-tolyl | hydrogen | hydrogen | white solid | 2 |
| 10 | 2,4-Dimethylphenyl | hydrogen | hydrogen | yellow liquid | 2 |
| 11 | 2-Chloro-6-fluorophenyl | hydrogen | hydrogen | colourless liquid | 2 |
| 12 | 2,6-Difluorophenyl | hydrogen | hydrogen | pale yellow solid | 2 |
| 13 | 2-Fluoro-4-chlorophenyl | hydrogen | hydrogen | pale yellow solid | 2 |
| 14 | 2,4-Difluorophenyl | hydrogen | hydrogen | yellow solid | 2 |
| 15 | 4-Fluoro-2-chlorophenyl | hydrogen | hydrogen | whitish solid | 2 |
| 16 | 2,4-Dichlorophenyl | hydrogen | methyl | liquid | 1,4 |
| 17 | 2,4-Dichlorophenyl | hydrogen | ethyl | liquid | 1,4 |
| 18 | 2,4-Dichlorophenyl | hydrogen | isopropyl | colourless liquid | 2 |
| 19 | 2,4-Dichlorophenyl | hydrogen | tert-butyl | yellow liquid | 2 |
| 20 | p-Tolyl | hydrogen | methyl | slightly yellow liquid | 2 |
| 21 | 2-Fluoro-4-chlorophenyl | hydrogen | methyl | yellowish liquid | 2 |
| 22 | 2,4-Dichlorophenyl | methyl | methyl | | 3 |
| 23 | 2,4-Dichlorophenyl | hydrogen | 1-methoxy-1-methylethyl | yellow liquid | 5 |
| 24 | o-Tolyl | hydrogen | 1-methoxy-1-methylethyl | yellow liquid | 5 |
| 25 | 2,4-Dimethylphenyl | hydrogen | 1-methoxy-1-methylethyl | yellow liquid | 5 |
| 26 | 2-Chloro-6-fluorophenyl | hydrogen | 1-methoxy-1-methylethyl | yellow liquid | 5 |
| 27 | 2,6-Difluorophenyl | hydrogen | 1-methoxy-1-methylethyl | yellow liquid | 5 |
| 28 | 4-Chloro-2-fluorophenyl | hydrogen | 1-methoxy-1-methylethyl | yellow liquid | 5 |
| 29 | 2,4-Difluorophenyl | hydrogen | 1-methoxy-1-methylethyl | reddish liquid | 5 |
| 30 | 4-Chloro-2-fluorophenyl | hydrogen | 1-(n-butoxy)-1-methylethyl | yellow liquid | 6 |
| 31 | 2-Chloro-4-fluorophenyl | hydrogen | 1-ethyl-1-methoxybutyl | yellow liquid | 6 |
| 32 | 2-Chloro-4-fluorophenyl | hydrogen | 1-(n-butoxy)-1-methylethyl | yellow liquid | 6 |
| 33 | 4-Chloro-2-fluoro- | hydrogen | 1-ethyl-1-methoxybutyl | yellow liquid | 6 |
| 34 | 2,4-Dichlorophenyl-phenyl | hydrogen | benzyl | yellow liquid | 2 |
| 35 | 2,4-Dichlorophenyl | hydrogen | 2,6-dichlorobenzyl | yellow liquid | 2 |
| 36 | 2-Fluoro-6-chlorophenyl | hydrogen | benzyl | yellow liquid | 2 |
| 37 | 2,4-Dichlorophenyl | hydrogen | 4-Nitrobenzyl | yellow liquid | 2 |
| 38 | 2,4-Dichlorophenyl | hydrogen | allyl | yellow liquid | 2 |

TABLE 1-continued

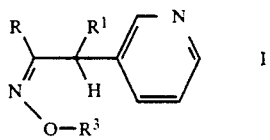

| Example | R | R¹ | R³ | Physical data | Method of Example |
|---|---|---|---|---|---|
| 39 | 2,4-Dichlorophenyl | hydrogen | propargyl | yellow liquid | 2 |
| 40 | 2,4-Dichlorophenyl | methyl | propargyl | yellow liquid | 3 |
| 41 | 2,4-Dichlorophenyl | hydrogen | phenyl | liquid | 2 |

EXAMPLE 42

0.55 g of sodium hydride dispersion (50% in oil) and then 2.20 g of 2-(4-fluorophenoxy)ethyl bromide are added with stirring to a solution of 2.81 g of 2',4'-dichloro-2-(3-pyridyl)acetophenone oxime in 20 ml of dimethylformamide. The reaction mixture is heated to 100° C. and stirred at this temperature for 1 hour. It is then cooled to room temperature and poured onto ice. The aqueous mixture is extracted with methylene chloride, and the organic phase is washed twice with water, dried over anhydrous magnesium sulfate and evaporated under reduced pressure. After chromatography on silica gel using n-hexane/ethyl acetate (7:3) as the eluent, 2',4'-dichloro-2-(3-pyridyl)acetophenone O-[2-(4-fluorophenoxy)ethyl]oxime is obtained as an E/Z isomer mixture in the form of a slightly yellow oil.

EXAMPLE 43

A solution of 1 g of 2',4'-dichloro-2-(3-pyridyl)acetophenone O-methyloxime in 20 ml of xylene is treated at room temperature with 0.61 g of 1,1-dimethoxycyclohexane and a spatula-tipful of finely pulverised Amberlyst ® A15, and the entire mixture is well stirred. It is then additionally stirred at an internal temperature of 100° C. for 24 hours. After cooling slightly, a further 0.61 g of 1,1-dimethoxycyclohexane and a spatula-tipful of Amberlyst ® A15 are added. The mixture is heated to 120° C. and stirred for a further 10 hours.

After cooling to room temperature, the mixture is filtered through Celite ® and the filtrate is taken up in diethyl ether. The ethereal solution is washed with water, dried over anhydrous magnesium sulfate and concentrated under reduced pressure, and the residue (1.62 g) is purified by chromatography on silica gel using n-hexane/ethyl acetate (7:3). (E)-2',4'-Dichloro-2-(3-pyridyl)acetophenone O-(1-methoxycyclohexyl)oxime [¹H-NMR (CDCl₃, 200 MHz): 4.114 ppm (s, CH₂—C₅H₄N)] is obtained first and then (Z)-2',4'-dichloro-2-(3-pyridyl)acetophenone O-(1-methoxycyclohexyl)oxime [¹H-NMR (CDCl₃, 200 MHz): 3.882 ppm (s, —CH₂—C₅H₄N)] as a yellow solid.

EXAMPLE 44

A solution of 10 g of 2',4'-dichloro-2-(3-pyridyl)acetophenone O-methyloxime in 100 ml of chloroform is treated at 0° C. with 7.2 g of m-chloroperbenzoic acid and then kept at about 4° C. in a refrigerator for 24 hours. The mixture is then diluted with 200 ml of chloroform and extracted with 250 ml of 10% potassium carbonate solution. The organic phase is dried over anhydrous sodium sulfate and concentrated. As a residue, 2',4'-dichloro-2-(3-pyridyl)acetophenone O-methyloxime-1-oxide is obtained as an E,Z isomer mixture in the form of a yellowish paste.

Table 2 contains further examples of compounds of the formula I. For these compounds, the process variant of the preparation process described in the present application for the compounds of the formula I used for preparation is indicated in each case.

| Ex. | Isomer form | Structure | Physical data | Method |
|---|---|---|---|---|
| 45 | E/Z | (4-chlorophenyl)(3-pyridylmethyl) ketone oxime | 136–137° C. (m.p.) | a |
| 46 | E/Z | (2,4-dichlorophenyl)(3-pyridylmethyl) ketone O-methyloxime·HCl | pale yellow solid | a |

-continued

| Ex. | Isomer form | Structure | Physical data | Method |
|---|---|---|---|---|
| 47 | E/Z | (2,4-dichlorophenyl)-C(=N-OMe)-CH(3-pyridyl)-CH2-C≡CH | dark red liquid | a |
| 48 | E/Z | (2,4-dichlorophenyl)-C(=N-OMe)-CH(3-pyridyl)-CH2-C(CH3)=CH2 | orange liquid | a |
| 49 | E/Z | (2,4-dichlorophenyl)-C(=N-OH)-CH(3-pyridyl)-CH2-C(CH3)=CH2 | 134–138° C. (m.p.) | a |
| 50 | E/Z | (2,4-dichlorophenyl)-C(=N-OMe)-CH2-(pyridin-3-yl, N-methylated) | 175–179° C. (m.p.) | a |
| 51 | E/Z | (2,4-dichlorophenyl)-C(=N-OMe)-CH2-(pyridin-3-yl, N-allyl) Br⁻ | 175–179° C. (m.p.) | a |
| 52 | E/Z | (2,4-dichlorophenyl)-C(=N-O-C(CH3)2-O-CH3)-CH2-(3-pyridyl) | yellow liquid | d |
| 53 | E | (4-methoxyphenyl)-C(=N-OMe)-CH2-(3-pyridyl) | slightly yellowish liquid | a |

-continued

| Ex. | Isomer form | Structure | Physical data | Method |
|---|---|---|---|---|
| 54 | E/Z | [structure: 2,4-dichlorophenyl-CH2-pyridyl ketoxime O-methyl, with pyridinium N-NH- tosylate] | grey solid | a |
| 55 | E/Z | [structure: 2-CF3-phenyl-C(=N-O-C(CH3)2-O-)-CH2-(3-pyridyl)] | yellowish liquid | d |
| 56 | E | [structure: 2,4-dimethylphenyl-C(=N-OH)-CH2-(3-pyridyl)] | brown crystals | b |
| 57 | E/Z | [structure: 2-chloro-6-fluorophenyl-C(=N-O-CH(O-)-2,4-dichlorophenyl)-CH2-(3-pyridyl)] | yellow liquid | d |
| 58 | E/Z | [structure: 2,4-dimethoxyphenyl-C(=N-O-CH3)-CH2-(3-pyridyl)] | b.p. 170° C./0.03 torr. yellow liquid | a |
| 59 | E/Z | [structure: 2,4-dimethoxyphenyl-C(=N-OH)-CH2-(3-pyridyl)] | 139–141.5° C., beige crystals | b |
| 60 | E/Z | [structure: 2,4-dimethoxyphenyl-C(=N-O-C(CH3)2-O-)-CH2-(3-pyridyl)] | brown resin | d |

-continued

| Ex. | Isomer form | Structure | Physical data | Method |
|---|---|---|---|---|
| 61 | E/Z | 2,4-bis(CF₃)-phenyl-CH₂-pyridin-3-yl ketone O-methyloxime | yellow solid | a |
| 62 | E/Z | 2,4-difluorophenyl-CH₂-pyridin-3-yl ketone O-(2-methoxyprop-2-yl)oxime | pale yellow oil | d |
| 63 | E/Z | 2-methoxyphenyl-CH₂-pyridin-3-yl ketone O-methyloxime | colourless liquid | a |
| 64 | Z | 2-chloro-4-fluorophenyl-CH₂-pyridin-3-yl ketone O-(3-methoxyhex-3-yl)oxime | yellow liquid | d |
| 65 | Z | 4-chloro-2-fluorophenyl-CH₂-pyridin-3-yl ketone O-(3-methoxyhex-3-yl)oxime | yellow liquid | d |
| 66 | E/Z | 2,4-dichlorophenyl-CH₂-pyridin-3-yl ketone O-(2-methoxyprop-2-yl)oxime | yellow liquid | d |
| 67 | E | 2,4-dichlorophenyl-CH₂-pyridin-3-yl ketone O-benzyloxime | yellow liquid | b |

-continued

| Ex. | Isomer form | Structure | Physical data | Method |
|---|---|---|---|---|
| 68 | Z | 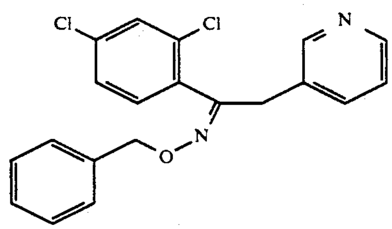 | yellow liquid | b |
| 69 | E/Z | 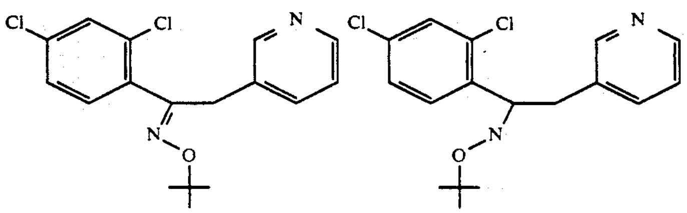 | yellow liquid | b |
| 70 | E | 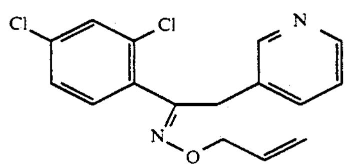 | yellow liquid | b |
| 71 | Z | 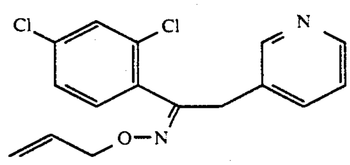 | yellow liquid | b |
| 72 | Z | 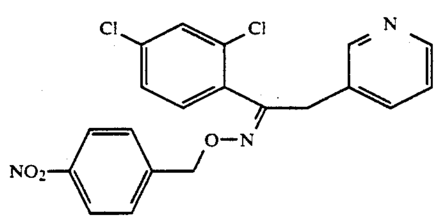 | yellow liquid | b |
| 73 | E/Z | 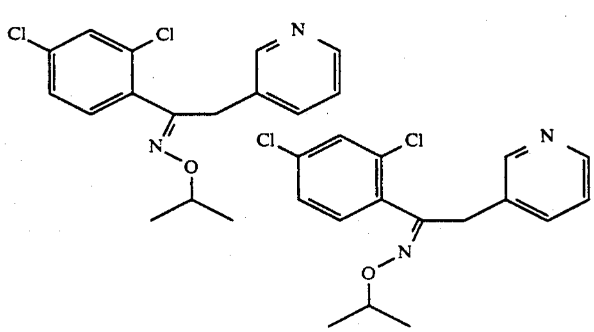 | yellow liquid | b |

-continued

| Ex. | Isomer form | Structure | Physical data | Method |
|---|---|---|---|---|
| 74 | E/Z | 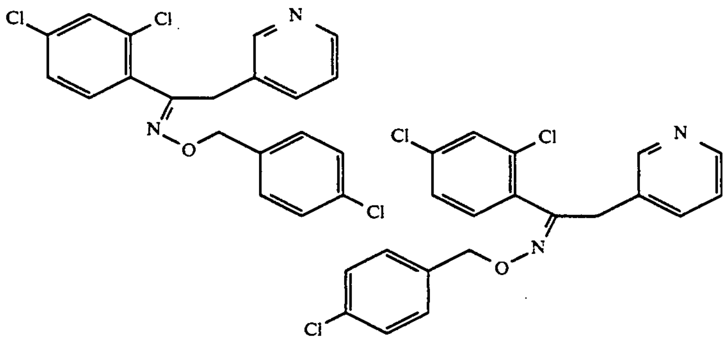 | yellow liquid | b |
| 75 | Z | 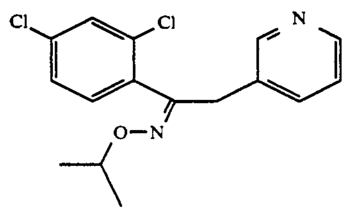 | yellow liquid | b |
| 76 | Z | 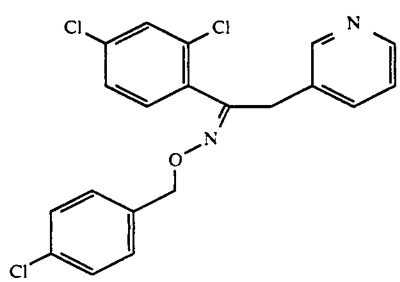 | yellow liquid | b |
| 77 | E | 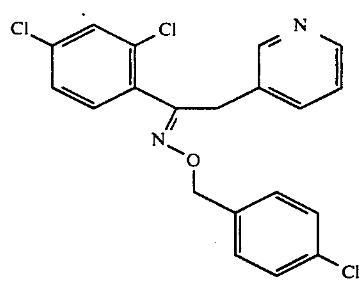 | yellow liquid | b |
| 78 | E | 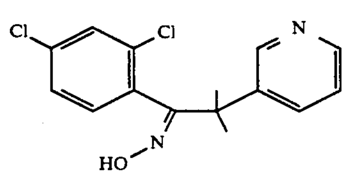 | 203–205° C. (m.p.), white crystals | b |
| 79 | E | 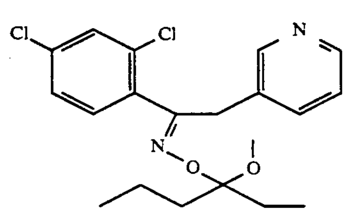 | yellowish liquid | d |

-continued

| Ex. | Isomer form | Structure | Physical data | Method |
|---|---|---|---|---|
| 80 | Z | 2,4-dichlorophenyl-C(=N-O-C(OMe)(Et)(nPr))-CH2-(3-pyridyl) | yellowish liquid | d |
| 81 | E | 2,4-dichlorophenyl-C(=N-O-CH(OEt)-iPr)-CH2-(3-pyridyl) | yellowish liquid | d |
| 82 | Z | 2,4-dichlorophenyl-C(=N-O-CH(OEt)-iPr)-CH2-(3-pyridyl) | yellowish liquid | d |
| 83 | E | 2,4-dichlorophenyl-C(=N-O-C(OMe)(Me)-CH2-OMe)-CH2-(3-pyridyl) | yellowish liquid | d |
| 84 | E | 2,4-dichlorophenyl-C(=N-O-CH(OMe)-Ph)-CH2-(3-pyridyl) | yellowish liquid | d |
| 85 | E | 4-bromophenyl-C(=N-OH)-CH2-(3-pyridyl) | 137–140° C. (m.p.), yellowish crystals | b |
| 86 | E | 2,4-dichlorophenyl-C(=N-O-C(Me)2-OEt)-CH2-(3-pyridyl) | yellow liquid | d |

-continued

| Ex. | Isomer form | Structure | Physical data | Method |
|---|---|---|---|---|
| 87 | Z | (2,4-dichlorophenyl)(pyridin-3-ylmethyl) ketone O-(1-ethoxy-1-methylethyl)oxime | yellow amorphous solid | d |
| 88 | E | (2,4-dichlorophenyl)(pyridin-3-ylmethyl) ketone O-(1-methoxy-1-methylnonyl)oxime | yellowish liquid | d |
| 89 | Z | (2,4-dichlorophenyl)(pyridin-3-ylmethyl) ketone O-(1-methoxy-1-methylnonyl)oxime | yellowish liquid | d |
| 90 | E/Z | (2-chloro-4-fluorophenyl)(pyridin-3-ylmethyl) ketone O-tert-butyl oxime | yellow liquid | b |
| 91 | E | (2,4-dichlorophenyl)(pyridin-3-ylmethyl) ketone O-(1-hexyloxy-1-methylnonyl)oxime | yellow liquid | d |
| 92 | E/Z | (2,4-dichlorophenyl)[1-(pyridin-3-yl)ethyl] ketone O-(1-ethoxy-2-methylpropyl)oxime | yellow liquid | d |

-continued

| Ex. | Isomer form | Structure | Physical data | Method |
|---|---|---|---|---|
| 93 | E | 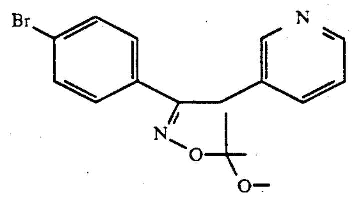 | yellow liquid | d |
| 94 | E/Z | 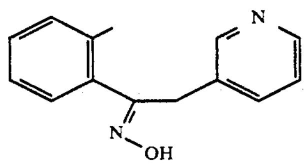 | 108–110° C. (m.p.), yellow crystals | b |
| 95 | E | 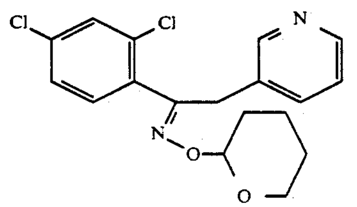 | yellow liquid | b |
| 96 | Z | 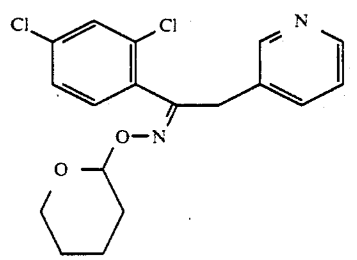 | yellow liquid | b |
| 97 | E | 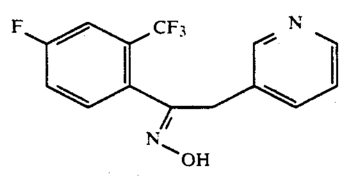 | 150–152° C. (m.p.), colourless crystals | b |
| 98 | E | 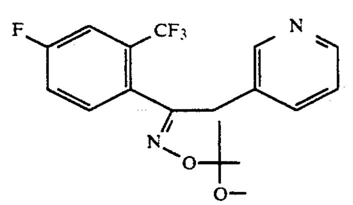 | yellow liquid | d |

II. Formulation examples

EXAMPLE F1

Granules, particularly suitable for use in paddy rice crops, contain the following constituents:

| | |
|---|---|
| Active ingredient (compound of the formula I or N-oxide thereof or acid addition salt of the compound I or of the N-oxide) | 50 g/kg |
| Dipropylene glycol monomethyl ether | 50 g/kg |
| Montmorillonite carrier granules. 24/48 mesh size | 900 g/kg |

For preparation, the active ingredient is intensively mixed with the carrier liquid (dipropylene glycol monomethyl ether). This solution is then sprayed onto the initially introduced carrier granules in a mixer in order to ensure a uniform impregnation of the carrier.

These granules are applied directly using a suitable granule application device.

EXAMPLE F2

A wettable powder contains the following constituents:

|  | Percent by weight |
| --- | --- |
| Active ingredient (compound of the formula I or N-oxide thereof or acid addition salt of the compound I or of the N-oxide) | 25 |
| Hydrated silica (auxiliary carrier) | 20 |
| Sodium lauryl sulfate (wetting agent) | 2 |
| Sodium lignosulfonate (dispersant) | 4 |
| Kaolin (carrier) | 49 |
|  | 100 |

Those compounds I, N-oxides or acid addition salts which are liquid at room temperature or have a relatively low melting point, i.e. about 100° C. or less, are suitable in particular as active ingredients for this formulation.

For preparation, the liquid or molten active ingredient is first sprayed onto the initially introduced silica in a powder mixer. The other constituents are then admixed, and the entire mixture is finely ground using a pinned-disc mill or comparable grinding appliance.

On stirring into water, the resulting wettable powder gives a fine suspension of the desired concentration which is suitable as a ready-to-use spray mixture.

EXAMPLE F3

An emulsifiable concentrate contains the following constituents:

| Active ingredient (compound of the formula I or N-oxide thereof or acid addition salt of the compound I or of the N-oxide) | 250 g/l |
| --- | --- |
| Nonylphenol polyethoxylate (non-ionic emulsifier) | 50 g/l |
| Calcium dodecylbenzenesulfonate (anionic emulsifier) | 25 g/l |
| Mixture of alkylbenzenes (solvent) to | 1000 ml |

The active ingredient and the emulsifiers are dissolved in the solvent with stirring. The resulting emulsifiable concentrate can be emulsified in water and thus gives a ready-to-use spray mixture of the desired concentration.

BIOLOGICAL EXAMPLES

EXAMPLE B1

Pre-emergent herbicide action

In a greenhouse, immediately after sowing the test plants (a number of weeds, both monocotyledon and dicotyledon) in seed trays, the soil surface is treated with an aqueous spray mixture corresponding to an application rate of 3 kg of active ingredient/hectare.

The test substances are preferably formulated as an emulsifiable concentrate (EC) and diluted to the desired concentration immediately before application in water. Insoluble substances are formulated as a wettable powder (WP) by means of kaolin as the inert carrier. This wettable powder is suspended in water immediately before application.

The dosages in g of active substance/ha relate to the soil surface in the containers, if not stated otherwise. The spray volume is 500 l/ha.

The seeds of the plants are sown in plastic plant pots of various sizes using heat-sterilised (steamed) soil (agricultural soil, 2.6% peat, 20% clay, 30% silt, 47% sand). The plants are kept in a greenhouse at moderate temperature (17°-25° C. in the winter, 18°-35° C. in the summer) (air humidity 30-90%). The length of the photo period is 13 to 16 hours/day, if necessary artificial light (15,000 to 18,000 lux) is switched on. The artificial illumination is also automatically activated in the case of inadequate daylight intensity.

After 3 weeks, the herbicide activity is evaluated using a ten-stage (10=complete damage, 0=no activity) linear assessment scheme in comparison to an untreated control group.

In this test, the compounds of the formula I described in the examples show potent herbicide action.

EXAMPLE B2

Post-emergent herbicide action (contact herbicide)

A number of weeds, both monocotyledon and dicotyledon, were treated with an aqueous active ingredient dispersion in a dosage of 3 kg of active substance per hectare after emergence (in the 4- to 6-leaf stage).

The test substances are preferably formulated as an emulsifiable concentrate (EC) and diluted to the desired concentration immediately before application in water. Insoluble substances are formulated as a wettable powder (WP) by means of kaolin as the inert carrier. This wettable powder is suspended in water immediately before application.

The dosages in g of active substance/ha relate to the soil surface in the containers, if not stated otherwise. The spray volume is 500 l/ha.

The seeds of the plants are sown in plastic plant pots of various sizes using heat-sterilised (steamed) soil ("Optima" soil, 80% peat, 20% loess). The plants are kept in a greenhouse at moderate temperature (17°-25° C. in the winter, 18°-35° C. in the summer) (air humidity 30-90%). The length of the photo period is 13 to 16 hours/day, if necessary artificial light (15,000 to 18,000 lux) is switched on. The artificial illumination is also automatically activated in the case of inadequate daylight intensity.

After 3 weeks, the herbicide action is evaluated using a ten-stage (10=complete damage, 0=no action) linear assessment scheme in comparison to an untreated control group.

In this test too, the compounds described in the examples show potent herbicide action.

EXAMPLE B3

Herbicide action for paddy rice

The seeds of the plants are sown in plastic beakers or boxes of various sizes closed at the bottom, using fertilised soil. The soil is heat-sterilised (steamed) and contains about 80% (w/v) of loam and 20% of peat and also 0.05% of Nutricote (16/10/10) and 0.05% of "Plantamaag" as a fertiliser. The plants are kept in a special greenhouse compartment at high temperature (20°-35° C.) and high air humidity (60-80%); the latter is kept constant using a sprinkler unit. The length of the photo period is 13 to 16 hours/day, if necessary artificial light (15,000 to 18,000 lux) is switched on. The artificial illumination is also automatically activated in the case of inadequate daylight intensity.

The test substances are preferably formulated as an emulsifiable concentrate (EC) and diluted to the desired concentration immediately before application in water. Insoluble substances are formulated as a wettable powder (WP) by means of kaolin as an inert carrier. This wettable powder is suspended in water immediately before application.

The dosages in g of active substance/ha relate to the soil surface in the containers, if not stated otherwise. The spray volume is 500 l/ha.

The tests are evaluated after 3 or 4 weeks (post-emergence or pre-emergence treatment respectively) using a ten-stage(10=complete damage, 0=no action) linear assessment scheme in comparison to an untreated control group.

Examples of the good selective herbicidal action of the compounds of the formula I described in the examples of the present application are shown in Table 3:

TABLE 3

| | Herbicidal action in paddy rice (pre-emergence), application rate 3 kg/ha: | |
|---|---|---|
| Example: | Isomeric form: | *Echinochloa crus-galli* | Rice *Oryza sativa* |
| 6 | E/Z | 9 | 0 |
| 17 | | 10 | 0 |
| 20 | E | 10 | 1 |
| 31 | Z | 10 | 0 |
| 50 | E | 10 | 1 |
| 69 | E/Z | 10 | 0 |
| 73 | E/Z | 10 | 0 |
| 77 | E/Z | 10 | 0 |
| 80 | E/Z | 10 | 1 |
| 97 | E/Z | 10 | 1 |

What is claimed is:

1. A method of controlling grassy weeds, which comprises applying to said weeds or their locus an herbicidally effective amount of an active substance of the formula I

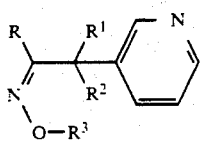

in which R is a substituted or unsubstituted phenyl group of the formula

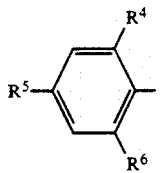

$R^1$ and $R^2$ independently of one another are hydrogen, $C_n$alkyl, $C_n$alkenyl or $C_n$alkynyl, where n is a number from 1–4 for $C_n$alkyl and 2–4 for $C_n$alkenyl or $C_n$alkynyl, with the proviso that one of $R^1$ or $R^2$ is hydrogen if n is greater than 2, $R^3$ is hydrogen or $C_{1-10}$alkyl; or $C_{3-10}$alkoxyalkyl or $C_{3-10}$alkylthioalkyl each containing an alkylene chain of at least two carbon atoms before the oxygen or sulfur atom thereof; phenyl or phenyl substituted by halogen, hydroxyl, $C_{1-3}$alkyl, $C_{1-3}$alkoxy, trifluoromethyl, nitro or cyano; phenyl-$C_{1-3}$alkyl or phenyl-$C_{1-3}$alkyl, which phenyl group is substituted by halogen, hydroxyl, $C_{1-3}$alkyl, $C_{1-3}$alkoxy, trifluoromethyl, nitro or cyano; $C_{3-6}$alkenyl; $C_{3-6}$alkynyl; or a group

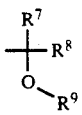

$R^4$ is hydrogen or fluorine, $R^5$ and $R^6$ independently of one another are hydrogen, halogen, $C_{1-4}$alkyl or trifluoromethyl, $R^7$ and $R^8$ independently of one another are hydrogen, $C_{1-6}$alkyl, $C_{3-6}$alkenyl or $C_{3-6}$alkynyl and $R^9$ is $C_{1-10}$alkyl; or $C_{3-6}$alkoxyalkyl or $C_{3-6}$alkylthioalkyl each containing an alkylene chain of at least two carbon atoms before the oxygen or sulfur atom thereof; phenyl-$C_{1-3}$alkyl or phenyl-$C_{1-3}$alkyl which phenyl group is substituted by halogen, hydroxyl, $C_{1-3}$alkyl, $C_{1-3}$alkoxy, trifluoromethyl, nitro or cyano; $C_{3-6}$cycloalkyl which is unsubstituted, monosubstituted or polysubstituted by $C_{1-3}$alkyl; $C_{3-10}$alkenyl; $C_{3-10}$alkynyl; or phenyl or phenyl which is substituted by halogen, hydroxyl, $C_{1-3}$alkyl, $C_{1-3}$alkoxy, trifluoromethyl, nitro or cyano; where the group (b) is not intended to include the $C_{3-10}$alkoxyalkyl group already defined above in $R^3$, or an N-oxide or acid addition salt of said compound of formula I or its corresponding N-oxide.

2. A method according to claim 1, in which R is 2-chloro-4-fluorophenyl, 4-chloro-2-fluorophenyl, 2,4-dichlorophenyl, 2-chloro-6-fluorophenyl or 2,6-difluorophenyl.

3. A method according to claim 1, which comprises applying an herbicidally effective amount of an active substance of the formula I in which $R^1$ and $R^2$ independently of one another are hydrogen or $C_{1-4}$alkyl.

4. A method according to claim 1, in which $R^3$ is tert-butyl or a group (b).

5. A method according to claim 1, in which $R^3$ is tert-butyl or a group (b) in which $R^7$, $R^8$ and $R^9$ are in each case methyl or $R^7$ is ethyl, $R^8$ is n-propyl and $R^9$ is methyl.

6. A method according to claim 1, which contains, as compound(s) of the formula I, at least one compound selected from the group comprising 2',4'-dichloro-2-(3-pyridyl)acetophenone O-(tert-butyl)-oxime, 2',4'-dichloro-2-(3-pyridyl)acetophenone O-(1-methoxy-1-methylethyl)oxime, 2'-chloro-4'-fluoro-2-(3-pyridyl)acetophenone O-(1-methoxy-1-methylethyl)oxime 2',6'-difluoro-2-(3-pyridyl)acetophenone O-(1-methoxy-1-methylethyl)oxime 4'-chloro-2'-fluoro-2-(3-pyridyl)acetophenone O-(1-methoxy-1-methylethyl)oxime and 2'-chloro-4'-fluoro-2-(3-pyridyl)acetophenone O-(1-ethyl-1-methoxy-n-butyl)oxime.

7. A method according to claim 1, which contains, as compound(s) of the formula I, at least one compound selected from the group consisting of 2',4'-dichloro-2-methyl-2-(3-pyridyl)propiophenone O-(1-methoxy-1-methylethyl)oxime, 2'-chloro-4'-fluoro-2-methyl-2-(3-pyridyl)propiophenone O-(1-methoxy-1-methylethyl)oxime, 2',4'-dichloro-2-(3-pyridyl)acetophenone O-(1-ethoxyethyl)oxime, 2'-chloro-4'-fluoro-2-(3-pyridyl)acetophenone O-(1-ethoxyethyl)oxime, 2',4'-dichloro-2-(3-pyridyl)acetophenone O-(1-methoxyethyl)oxime, 2'-chloro-4'-fluoro-2-(3-pyridyl)acetophenone O-(1-methoxyethyl)oxime, 2',4'-dichloro-2-(3-pyridyl)acetophenone O-(1-methoxypropyl)oxime, 2'-chloro-4'-fluoro-2-(3-pyridyl)acetophenone O-(1-methoxypropyl)oxime, 2',4'-dichloro-2-(3-pyridyl)propiophenone O-methoxymethyloxime, 2'-chloro-4'-fluoro-2-(3-pyridyl)propiophenone O-methoxymethyloxime.

8. A method according to claim 1, wherein an amount of active ingredient between 0.001 and 3 kg per hectare is applied.

* * * * *